(12) United States Patent
Levecq

(10) Patent No.: US 11,047,741 B2
(45) Date of Patent: Jun. 29, 2021

(54) METHOD FOR EVALUATING THE QUALITY OF THE MEASUREMENT OF A WAVEFRONT AND SYSTEMS IMPLEMENTING SUCH A METHOD

(71) Applicant: IMAGINE OPTIC, Orsay (FR)

(72) Inventor: Xavier Levecq, Gif-sur-Yvette (FR)

(73) Assignee: IMAGINE OPTIC, Orsay (FR)

( * ) Notice: Subject to any disclaimer, the term of this patent is extended or adjusted under 35 U.S.C. 154(b) by 0 days.

(21) Appl. No.: 16/481,413

(22) PCT Filed: Jan. 26, 2018

(86) PCT No.: PCT/EP2018/051970
§ 371 (c)(1),
(2) Date: Sep. 10, 2019

(87) PCT Pub. No.: WO2018/138269
PCT Pub. Date: Aug. 2, 2018

(65) Prior Publication Data
US 2019/0391020 A1     Dec. 26, 2019

(30) Foreign Application Priority Data

Jan. 27, 2017 (FR) ..................... 1750684

(51) Int. Cl.
*G01J 9/02*     (2006.01)
(52) U.S. Cl.
CPC ....... *G01J 9/0215* (2013.01); *G01J 2009/028* (2013.01)
(58) Field of Classification Search
CPC ...... G01J 9/0215; G01J 2009/028; G01J 9/00; G01J 2009/002; A61B 3/1015
See application file for complete search history.

(56) References Cited

U.S. PATENT DOCUMENTS 6,052,180 A * 4/2000 Neal .................. G01J 9/00
                                                     250/201.9
6,577,403 B1    6/2003 Primot et al.
(Continued)

FOREIGN PATENT DOCUMENTS

EP        1 061 349 A1    12/2000
WO      01/28409 A1    4/2001

OTHER PUBLICATIONS

Jerome Primot, "Theoretical description of Shack-Hartmann wavefront sensor", 2003, Optics Communications 222, p. 81-92 (Year: 2003).*

(Continued)

*Primary Examiner* — Jonathan M Hansen
(74) *Attorney, Agent, or Firm* — Osha Bergman Watanabe & Burton LLP

(57) ABSTRACT

A method for evaluating the quality of the measurement of an optical wavefront, said measurement being obtained by means of a wavefront analyzer by direct measurement, the method comprising:
the acquisition (10) of an optoelectronic signal for the measurement of the wavefront by means of a wavefront sensor, said sensor comprising a two-dimensional detector;
the determination (11) on the basis of said optoelectronic signal of at least one parameter characteristic of a parasitic component of the optoelectronic signal;
the evaluation (12) of a quality factor of the measurement of the wavefront as a function of said at least one parameter characteristic of the parasitic component of the signal;
the display (13) to a user of a level of quality of the measurement as a function of said quality factor.

15 Claims, 7 Drawing Sheets

(56) References Cited

U.S. PATENT DOCUMENTS

2005/0036153 A1  2/2005  Joannes
2010/0310130 A1  12/2010 Beghuin et al.
2014/0063455 A1  3/2014  Zhou et al.

OTHER PUBLICATIONS

International Search Report issued in PCT/EP2018/051970 dated May 15, 2018 (7 pages).
Written Opinion of the International Searching Authority issued in PCT/EP2018/051970 dated May 15, 2018 (12 pages).
Nightingale, A.M. et al.; "Shack-Hartmann wavefront sensor image analysis: a comparison of centroiding methods and image-processing techniques"; Optical Engineering, vol. 52, No. 7, Jul. 2013, pp. 1-21 (22 pages).
Platt et al.; "History and Principles of Shack-Hartman Wavefront Sensing;" Journal of Refractive Surgery; vol. 17; Sep./Oct. 2001 (5 pages).
Nightingale et al.; "Shack-Hartman wavefront sensor image analysis: a comparison of centroiding methods and image processing techniques;" Optical Engineering; vol. 52(7); Jul. 2013 (22 pages).

\* cited by examiner

METHOD FOR EVALUATING THE QUALITY OF THE MEASUREMENT OF A WAVEFRONT AND SYSTEMS IMPLEMENTING SUCH A METHOD

STATE OF THE ART

Technical Field of the Invention

This description relates to a method for evaluating the quality of the measurement of an optical wavefront, and more specifically the measurement of a wavefront obtained by means of a wavefront analyzer by direct measurement. This description also includes systems of wavefront analysis by direct measurement of the wavefront using such a method.

State of the Art

The phase analysis of an optical wavefront (referred to simply in this description as "optical wavefront analysis (or measurement)") has many applications; for example, the qualification of light sources (laser sources, laser diodes, LEDs) or refractive or reflective optical components, such as imaging lens, mirrors, filters, windows, etc. or the control of deformable optical components, for example deformable mirrors, liquid crystal valves, liquid lenses and more generally any phase modulator used in active optics, adaptive optics or for beam shaping.

In particular, there are known techniques for wavefront analysis by direct measurement of the wavefront (as opposed to interferometric techniques using the interference of the wavefront to be analyzed with a reference wavefront); the techniques of wavefront analysis by direct measurement allow the determination of local wavefront slopes (i.e. the first derivatives of the wavefront) and are generally based on an analysis of the variation in the angle of the light path using a wavefront sensor comprising a set of one or more optical element(s) and a generally two-dimensional detector.

Thus, among the techniques of wavefront analysis by direct measurement, we can mention, for example and in a non-exhaustive way, the techniques known as Hartmann and Shack Hartmann, lateral shearing interferometry, deflectometry by moiré image, Schlieren's method, etc. A brief description of these techniques is provided below.

In Hartmann and Shack Hartmann techniques, the wavefront sensor includes a matrix of holes or microlenses positioned in front of a, usually two-dimensional, detector at a distance typically of a few millimeters. In this technique, an array of spots is formed on the detector by the matrix of holes or microlenses. The measurements of the displacements of each of these spots with respect to reference positions in the presence of a planar wavefront without aberrations are directly proportional to the local slopes of the measured wavefront, i.e. directly proportional to the derivative of the aberrations present on the measured wavefront. The proportionality coefficient is equal to the distance between the matrix of holes or microlenses and the detector. The numerical integration of these local slopes makes it possible to obtain the phase of the measured wavefront (see for example "*Principles and History of Shack-Hartmann*", Journal of Refractive Surgery Volume 17 September/October 2001).

Lateral shearing interferometry is described in U.S. Pat. No. 6,577,403, for example. According to this technique, several "daughter" waves are generated along different propagation axes from a diffraction grating illuminated by a "mother" wave and interfere after propagation; the interference pattern is recorded by a two-dimensional detector located for example a few millimeters behind the diffraction grating. The deformations of the interference pattern are proportional to the local slopes of the analyzed wavefront. The analysis of these deformations makes it possible to calculate the local slopes of the wavefront and to obtain, by integration, the phase of the wavefront.

In the technique known as moiré image deflectometry (see for example US20100310130), the wavefront sensor includes an array of patterns of variable intensities illuminated by a wave from a source with good spatial coherence; these patterns are deformed when the light wave passes through the optical element to be controlled; the deformations are recorded on a two-dimensional detector placed in a conjugated plane of the network of patterns of variable intensities. The analysis of these deformations makes it possible to trace the deflections suffered by the light rays when passing through the optical element to be controlled; these deflections are the local slopes of the wavefront which represent local derivatives of the optical aberrations introduced by the optical element to be controlled. The wavefront is calculated by integrating the local slopes thus measured.

In Schlieren's method (see for example US patent application 20050036153), the wavefront, after passing through the optical element to be measured, is focused in a focusing plane where there is a spatially variable optical density blade. The positions of the rays in the focusing plane being directly proportional to the angular deviation they have undergone when passing through the optical element to be measured, they undergo an intensity encoding when passing through the variable density blade. These rays are then imaged on a detector placed in a conjugated plane of the object to be measured. The signal level on each pixel reveals the attenuation suffered by the beam incident on this pixel, which makes it possible to know the angular deviation that this beam underwent during the passage of the optical element to be measured. The signal level map acquired by the two-dimensional detector therefore makes it possible to ascend the local slopes of the wavefront when passing through the optical element to be controlled.

The techniques of wavefront analysis of the wavefront by direct measurement are widely used, especially for the characterization of optical components, as they are generally simpler to implement than interferometric techniques (no use of a reference wavefront) and also allow the characterization of wavefronts from light sources. They also allow the analysis of wavefronts with higher amplitude deformations.

In the implementation of these techniques, however, the accuracy of the measurement of the wavefront obtained is difficult to verify by a user. Indeed, the conditions of implementation of the analysis system can disrupt the measurement of the wavefront without this being easily detected by the user. For example, a parasitic light source, whether extended or as a spot, a parasitic reflection on a diopter of an optical component to be analyzed or the presence of parasitic interference, can introduce a parasitic signal on the detector that can disturb the measurement of the local slopes of the wavefront and thus degrade the reconstruction of the wavefront.

A purpose of this description is to propose a method for evaluating the quality of the measurement of an optical wavefront obtained by means of a wavefront analyzer by direct measurement, in order to give a user a quality factor of the measurement performed, which allows same to estimate the reliability level of the measurement and to feedback, if necessary, on the conditions of implementation of the wavefront analysis.

SUMMARY OF THE INVENTION

In a first aspect, this description relates to a method for evaluating the quality of the measurement of an optical wavefront, said measurement being obtained by means of a wavefront analyzer by direct measurement, the method comprising the following steps:
- the acquisition of an optoelectronic signal for the measurement of the wavefront by means of a wavefront sensor, said sensor comprising a two-dimensional detector;
- the determination on the basis of said optoelectronic signal of at least one parameter characteristic of a parasitic component of the optoelectronic signal;
- the evaluation of a quality factor of the measurement of the wavefront as a function of said at least one parameter characteristic of the parasitic component of the signal;
- the display to a user of a level of quality of the measurement as a function of said quality factor.

The method for evaluating the quality of the measurement of the wavefront thus described makes it possible for a user to think that the measurement made on the basis of the optoelectronic signal used for the measurement itself is reliable. This allows on the one hand having a reliable quality factor for the measurement performed, and on the other hand it avoids the need to perform additional tests with specific tools, such as parasitic light measurement tests.

A parameter characteristic of a parasitic component of the optoelectronic signal may include, according to one or more exemplary embodiment(s), a signal measured in areas of the two-dimensional detector that are not covered by a signal useful for the measurement of the wavefront. The determination of such a parameter for the evaluation of a measurement quality factor is for example suitable in the case where parasitic signal sources are an ambient light, forming a non-uniform diffuse background signal on the two-dimensional detector, or a point light source with good spatial coherence, etc.

Thus, according to one or more exemplary embodiment(s), the determination on the basis of the optoelectronic signal of a parameter characteristic of a parasitic component of the signal may include the following steps:
- the identification of the areas of the detector not covered by a useful signal for the measurement of the wavefront;
- the determination of a parameter characteristic of a parasitic component of the signal on the basis of the signal measured in said areas.

Another parameter characteristic of a parasitic component of the optoelectronic signal may include, according to one or more exemplary embodiment(s), a subset of non-integrable components of local slope measurements called "non-integrable local slopes".

In this description, the quantities determined on the basis of the optoelectronic signal to measure the local slopes of the wavefront are referred to as "measured local slopes" or "raw local slopes", which can be determined in different ways depending on the technique chosen (Shack Hartmann, lateral shearing interferometry, moiré image deflectometry, Schlieren method, etc.), as recalled in the state-of-the-art description. At a given point, the measured local slope includes an integrable component which includes in particular the local slope of the wavefront which is ultimately sought and may also include a non-integrable component which, when it exists, can only be linked to a parasitic component of the optoelectronic signal, whatever its origin.

Thus, the presence of non-integrable components in the raw local slopes, called "non-integrable local slopes" in the description, is a very good parameter characteristic of a parasitic component of the optoelectronic signal and is therefore a very good indicator of the quality of the measurement. In particular, such a characteristic parameter for the evaluation of a measurement quality factor is suitable not only in the case where the parasitic signal results in a luminous flux on the detector covering areas outside those in which the useful signal for the measurement is located, but also in the case where the parasitic signal is located in areas in which the useful signal for the measurement is also located.

Thus, according to one or more exemplary embodiment(s), the determination of a parameter characteristic of a parasitic component of the optoelectronic signal may include the following steps:
- the calculation, on the basis of said optoelectronic signal, of raw local slopes at a given number of points and the determination, for each raw local slope, of a non-integrable component, thereby forming a subset of non-integrable local slopes.

According to one or more exemplary embodiment(s), the determination of said set of non-integrable local slopes includes: integrating said raw local slopes to obtain a reconstruction of a wavefront;
- the derivation of the thus reconstructed wavefront in order to determine, for each raw local slope, an integrable component, thus forming a subset of integrable local slopes at each of said points;
- the subtraction at each of said points of the local slopes integrable with the raw local slopes to obtain said subset of the non-integrable local slopes, said parameter characteristic of a parasitic component of the optoelectronic signal being determined on the basis of said subset of the non-integrable local slopes.

According to one or more exemplary embodiment(s), the quality factor can then be evaluated on the basis of a peak-valley value or a root mean square value (or "RMS" according to the Anglo-Saxon abbreviation "root mean square") of at least part of the local slopes that cannot be integrated.

According to one or more exemplary embodiment(s), the quality factor can also be evaluated on the basis of the power spectral density (or "PSD") of at least part of the local non-integrable slopes, or a combination of these parameters (RMS and PSD for example).

In a second aspect, this description relates to a method for analyzing an optical wavefront by direct measurement of the wavefront, comprising:
- the acquisition of an optoelectronic signal using a two-dimensional detector for measuring the wavefront;
- the reconstruction of the wavefront on the basis of said optoelectronic signal to obtain a measurement of the wavefront;
- the evaluation of the quality of said measurement of a wavefront using a method according to the first aspect.

A third aspect of this description is that it relates to systems for the analysis of an optical wavefront by direct measurement, including:
- a wavefront sensor provided with a two-dimensional detector for the acquisition of an optoelectronic signal allowing the measurement of the wavefront;

an optoelectronic signal processing unit for reconstructing the wavefront on the basis of said signal, said processing unit being further adapted for:

the determination, on the basis of said optoelectronic signal, of at least one parameter characteristic of a parasitic component of the signal;

the evaluation of a quality factor of the measurement of the wavefront as a function of said at least one parameter characteristic of the parasitic component of the signal;

a unit for displaying to a user a level of quality of the measurement as a function of said quality factor.

According to one or more exemplary embodiment(s), the wavefront sensor includes a matrix of microlenses positioned in front of a two-dimensional detector and the optoelectronic signal includes an array of spots formed by each of the microlenses illuminated by the wavefront to be measured.

According to one or more exemplary embodiment(s), the wavefront sensor includes a matrix of holes positioned in front of a two-dimensional detector and the optoelectronic signal includes an array of spots formed by each of the holes illuminated by the wavefront to be measured.

According to one or more exemplary embodiment(s), the wavefront sensor includes a phased array positioned in front of a two-dimensional detector and the optoelectronic signal includes an array of spots formed by the figure resulting from the interference of the waves generated by the phased array traversed by the wavefront to be measured.

BRIEF DESCRIPTION OF THE FIGURES

Other advantages and characteristics of the invention will appear upon reading the description, illustrated by the figures below.

For sake of consistency, identical elements are identified by the same references in the different figures.

DETAILED DESCRIPTION

Figure 1:
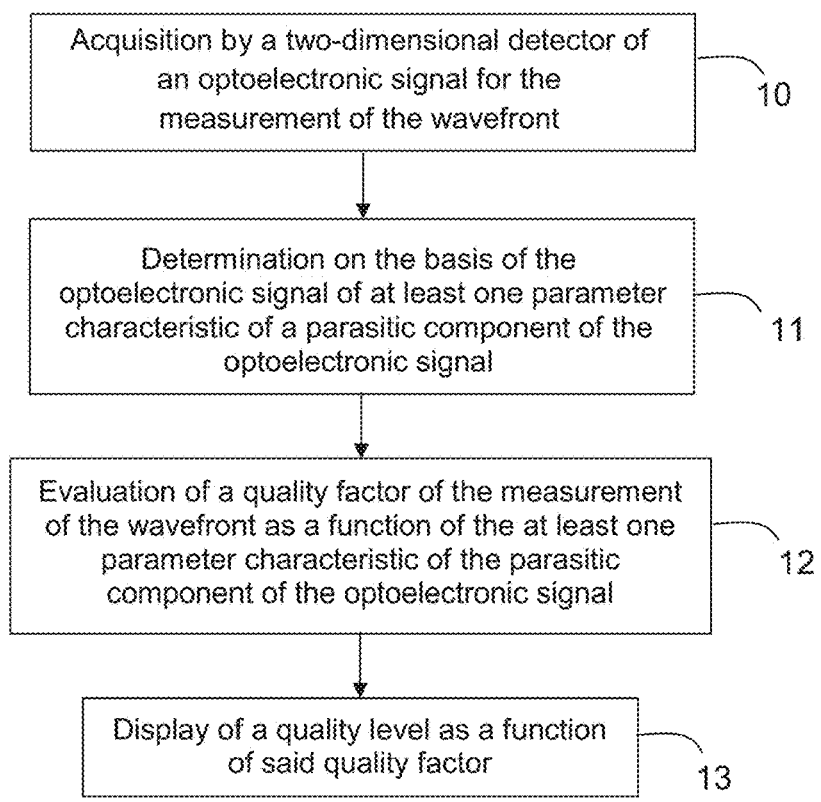
FIG. 1, a diagram illustrating steps of a method for evaluating the quality of the measurement of the optical wavefront according to this description.
Figure 2:
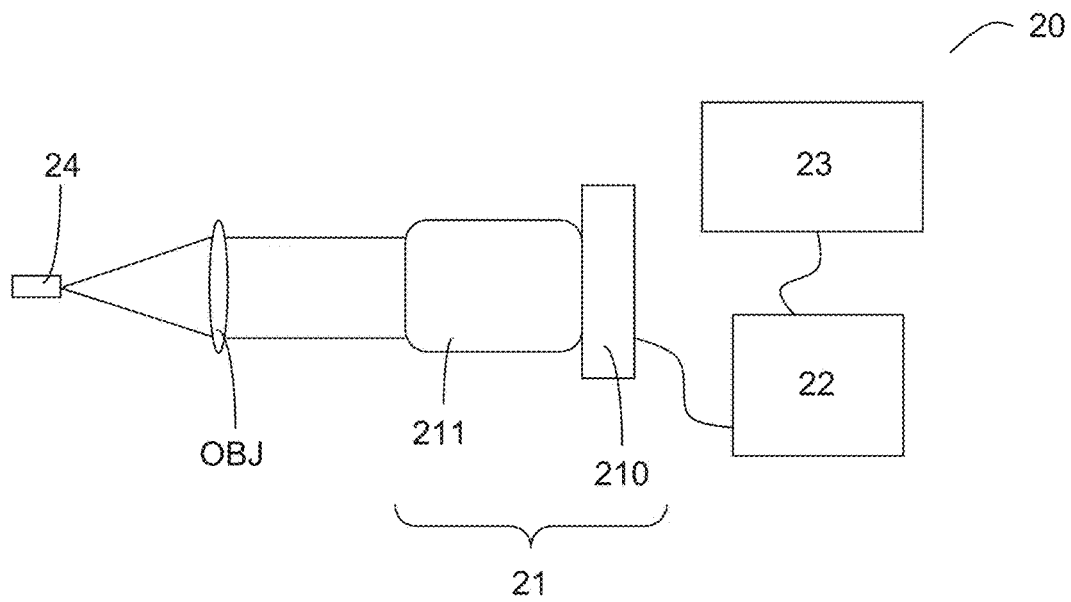
FIG. 2, a diagram illustrating an example of a system for the analysis of an optical wavefront by direct measurement according to this description.

FIGS. 1 and 2 generally illustrate steps of a method for evaluating the quality of measurement of an optical wavefront as well as a wavefront analysis system by direct measurement implementing such a method.

More precisely, the wavefront analysis system 20 illustrated on FIG. 2 includes a wavefront analyzer 21 with a two-dimensional detector 210 for the acquisition of an optoelectronic signal enabling the measuring of the wavefront and an assembly of one or more optical element(s) schematized as a single element referenced 211 in FIG. 2. The wavefront analysis system also includes a processing unit 22 adapted to the processing of the optoelectronic signal acquired by the detector 210 for reconstruction of the wavefront on the basis of said optoelectronic signal, and a display unit 23. The processing unit 22 is also suitable for the implementation of the method for evaluating the quality of the wavefront measurement according to this description, as described below, so that when the method for evaluating the quality is implemented, the "quality factor" of the measurement is displayed on the display unit 23, for example in the form of a colour from a colour code, or a number, etc.

In the example of FIG. 2, the wavefront analysis system 20 is suitable for characterizing an object OBJ that does not emit light itself; according to an exemplary embodiment, the wavefront analysis system 20 may also include a source of illumination 24 of the object. Alternatively, the object is illuminated by an external light source which does not belong to the analysis system. The measurement can be carried out in transmission (in the case of FIG. 2) but can also be carried out in reflection in the case of the analysis of a reflective system (e.g. a mirror). The object OBJ to be characterized is, for example, and not exhaustively, a refractive or reflective optical component, such as an imaging lens, a mirror, a filter, a porthole, etc.; the object OBJ may also be a deformable optical component, for example a deformable mirror, a liquid crystal valve, a liquid lens and more generally any phase modulator used in active optics, adaptive optics or for beam shaping. In this case, the analyzed wavefront is the wavefront from the illuminated object, the analysis of the wavefront allowing the optical characterization of the object. The light source 24 is for example a laser, a (fiber or not) laser diode, a (fiber or not) super-luminescent diode, a (fiber or not) LED or a hole illuminated by a lamp.

Of course, in the case where the object to be characterized is a light source (e.g. a laser source, a laser diode, a light-emitting diode or a LED), the implementation of the measurement does not need to provide a light source as shown in FIG. 2. The analyzed wavefront is indeed directly the wavefront emitted by the light source which is itself the object of the analysis.

FIG. 1 illustrates, according to an example, the steps of the method for evaluating the quality of the measurement of the wavefront according to this description, implemented for example by means of a wavefront analysis system as illustrated on FIG. 2.

The method comprises the acquisition (step 10) of an optoelectronic signal using a wavefront sensor for measuring the wavefront, the determination (step 11) on the basis of the optoelectronic signal of at least one parameter characteristic of a parasitic component of the optoelectronic signal, the evaluation (step 12) of a quality factor of the measurement of the wavefront as a function of said at least one parameter characteristic of the parasitic component of the signal, and the display (step 13) of a level of quality determined as a function of said quality factor, on a display unit as shown for example on FIG. 2.

This description also includes a method of wavefront analysis by direct measurement that incorporates the method for evaluating the quality of the wavefront measurement as described in FIG. 1.

As mentioned in the "State of the art" section, all the techniques of wavefront analysis by direct measurement have in common, in particular a measurement of the local slopes of the wavefront desired to be analyzed. When there is no parasitic signal, these local slopes correspond to the first derivatives of the wavefront phase that is desired to be reconstructed. More specifically, in the following description, it will be considered that a local slope measured at coordinates (i,j) in a measurement plane defined by an orthonormal reference system (x,y) (a "raw" local slope) can be described by a component along the x axis and a component along the y axis. All raw local slopes can therefore be represented as a table of slopes x ("tabX") and a table of slopes y ("tabY"). The raw local slope at the coordinate point (i,j) in the measurement plane will therefore have "tabX(i,j)" as a component along the x axis and "tabY(i,j)" as a component along the y axis. In the following description, the processings can be carried out from the table of slopes along the x-axis and/or the table of slopes along the y-axis.

To switch from the measured local slopes (raw local slopes) to the wavefront phase, a numerical integration of the raw local slopes is performed. There are several ways to digitally integrate a two-dimensional signal. This may be, for example, a so-called "zonal" integration, a description of which is presented in the article "*Wave-front estimation from wave-front slope measurements*" J. Opt. Soc. Am., Vol. 70, No. 8, August 1980.

The method for evaluating the quality of the measurement of the wavefront can be performed concurrently with the measurement of the wavefront itself, i.e. concomitantly with the reconstruction of the wavefront on the basis of the optoelectronic signal acquired by the detector. In this case, a user sees both the reconstructed wavefront and a value of the quality factor displayed at the same time, and the user thus thinks that the measurement performed is reliable.

The method for evaluating the quality of the wavefront measurement can also be postponed after the measurement of the wavefront itself. Indeed, once the optoelectronic signal has been acquired and saved, the user can start the evaluation of the quality factor at any time after having measured the wavefront, with no time limit.

Several parameters characteristic of a parasitic signal component can be determined on the basis of the optoelectronic signal acquired by the detector 210 to evaluate a measurement quality factor. The nature of the parameter may depend on the type of the parasitic signal. It will also be possible to combine these parameters.

Figure 3A:
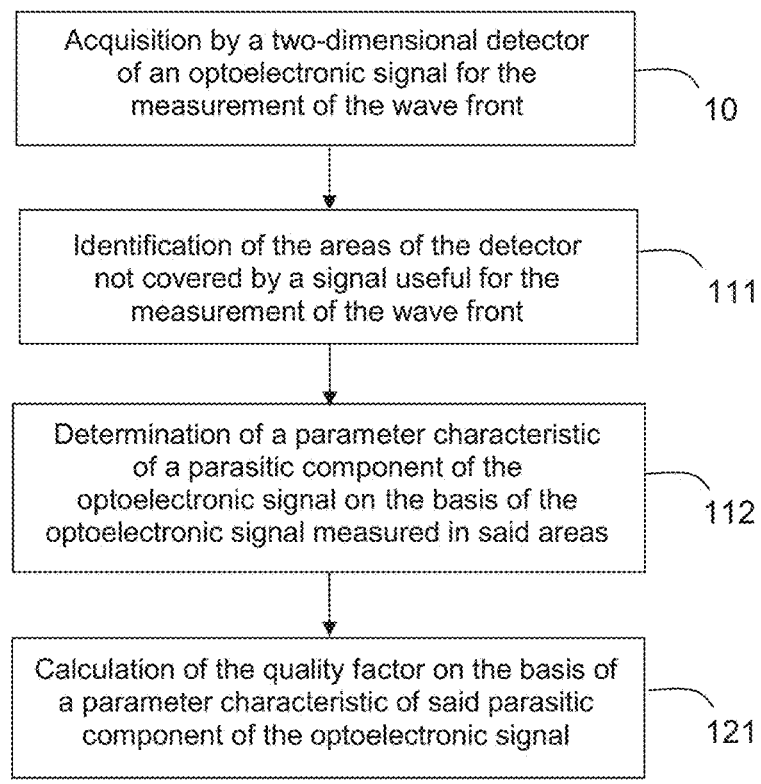
FIG. 3A, a diagram illustrating steps of a first example of a method for evaluating the quality of the measurement of the optical wavefront according to this description.
Figure 3B:
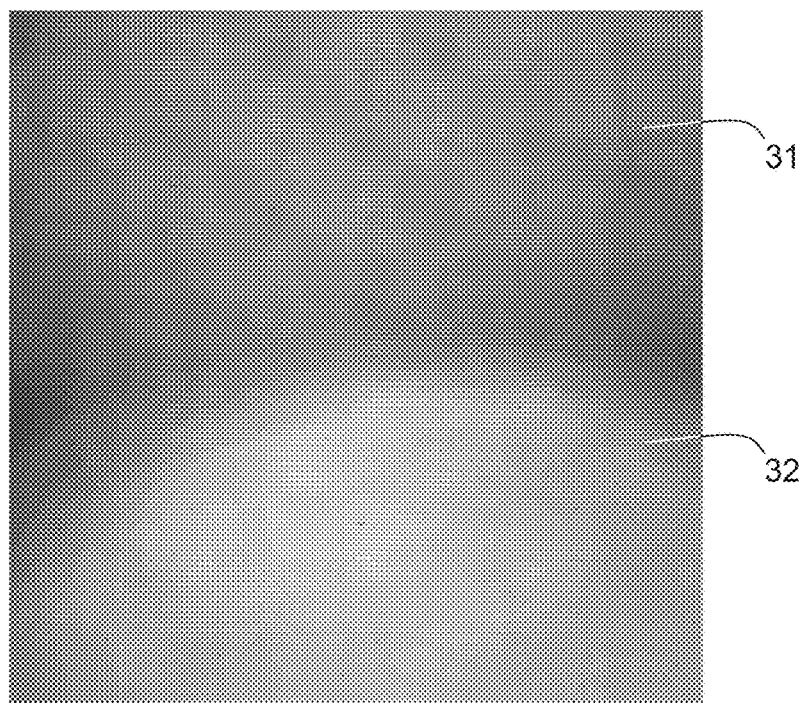
FIG. 3B, an example of an optoelectronic signal acquired by the detector showing an example of a parasitic signal identified during a step of the method illustrated in FIG. 3A and FIG. 3C a diagram illustrating a step of the method described on FIG. 3A.
Figure 3C:
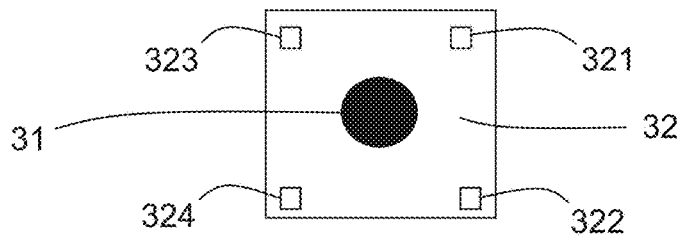

FIGS. 3A-3C on the one hand and FIGS. 4 to 7 on the other hand, thus illustrate two examples in which different parameters, both characteristic of a parasitic component of the signal, are identified.

FIG. 3A illustrates a first example of a method for evaluating the quality of the wavefront measurement according to this description, in which a signal is detected in the areas of the two-dimensional detector that are not covered by a signal useful for measuring the wavefront. Such a characteristic parameter for the evaluation of a measurement quality factor is suitable in particular in the case where parasitic signal sources are an ambient light, forming on the two-dimensional detector a non-uniform diffuse background signal, or a spot light source with good spatial coherence, etc.

The method as described on FIG. 3A includes, after the acquisition (step 10) of an optoelectronic signal for the measurement of the wavefront, a step 111 of identification on the basis of said optoelectronic signal of areas not covered by the signal useful for the measurement of the wavefront.

FIG. 3B represents, for example, the image acquired by a two-dimensional detector of a Shack Hartmann wavefront analyzer in the presence of a diffuse parasitic signal due to the ambient light of the room where the measurement was performed. The array of spots 31 represents the spots generated by the microlens matrix through which the wavefront to be analyzed passes. This array of spots 31 represents the useful signal. This figure clearly shows a diffuse and non-uniform parasitic flow due to the presence of a parasitic light due to the ambient lighting in the room. This signal is easily identifiable in areas of the two-dimensional detector not covered by the useful signal (the areas referenced 32). FIG. 3C schematically illustrates the area 31 representing the spot generated by a microlens (a useful signal) and the area 32 outside the area 31.

The method for evaluating the quality of the wavefront measurement then includes the determination (step 112) of a parasitic component on the basis of the optoelectronic signal measured in areas that are not covered by a useful signal for the wavefront measurement and the quality factor calculation (step 121) on the basis of at least one parameter characteristic of the parasitic component.

For example, in the case of a Hartmann Shack analyzer, the steps 111, 112 and 121 can be performed as follows:

Step 111: When calculating the local raw slopes from the spots formed by the microlens matrix, a given number of measurement areas of the parasitic signal around the spot formed by each microlens are identified on the optoelectronic signal from the detector. On FIG. 3C, these are for example 4 zones referenced 321, 322, 323, 324.

Step 112: For each of the spots, the value of the optoelectronic signal of the matrix detector is measured in the measurement areas of the parasitic signal 321, 322, 323, 324 and the average is calculated. A map of the amplitude of the parasitic flow corresponding to the parameter characteristic of the parasitic component of the signal is thus obtained.

Step 121: the quality factor is calculated, for example, by averaging the map of the parasitic flux amplitude obtained in step 112. In this example, the higher the value of the quality factor, the more the measurement will be declared as disturbed by the interfering signal to a user.

According to another example, still in the case of a Hartmann Shack analyzer, steps 111, 112 and 121 can be performed as follows:

Step 111: When calculating the raw local slopes from the spots formed by the microlens matrix, a given number of measurement areas of the parasitic signal 321, 322, 323, 324 around the spot 31 are identified on the basis of the optoelectronic signal from the detector, for example 4 as in the previous example.

Step 112: For each of the spots, the value of the optoelectronic signal of the matrix detector is measured in the measurement areas of the parasitic signal 321, 322, 323, 324 and the absolute value of the difference in the values of the optoelectronic signal in the areas taken 2 by 2 is calculated and averaged. This results in a map representing the non-uniformity of the parasitic signal around the useful signal, this map forming the parameter characteristic of the parasitic component of the signal.

Step 121: the quality factor is calculated by averaging, for example, the non-uniformity map of the interfering signal around the useful signal obtained in step 121. In this example, the higher the quality factor value, the more the measurement is declared disturbed by the interfering signal.

In all cases, "measurement quality" is displayed. For example, a discrete number of colours or numbers are associated with calculated values of the quality factor, indicating to the user what each colour or number corresponds to. Thus, for example, there can be 5 levels of the quality factor, corresponding respectively to excellent, good, average, bad, very bad quality. Depending on the level of the quality factor, a user may be recommended a number of measures to be taken to restore better measurement conditions. When the level of quality is not satisfactory, several improvements can be brought. For example:

Eliminate the ambient light (switch off the light in the room where the measurement is performed)

Hide the parasitic light sources that may, even partially, illuminate the detector of the wavefront analyzer. These interfering light sources may be, for example, a computer monitor, the on/off indicators of electronic devices, a desk lamp, etc.

Acquire a background image that will be subtracted from the acquisitions made to measure the wavefront. One way to acquire a background image is to acquire an image with the detector of the wavefront analyzer by turning off or hiding the light source generating the beam used to perform the measurement (source 24 of FIG. 2 for example).

Although the above exemplary calculation and display of the measurement level of quality have been given in the particular case of a Shack-Hartmann analyzer, they can easily be transposed to any one of the wavefront analyzers by direct measurement.

Figure 4:
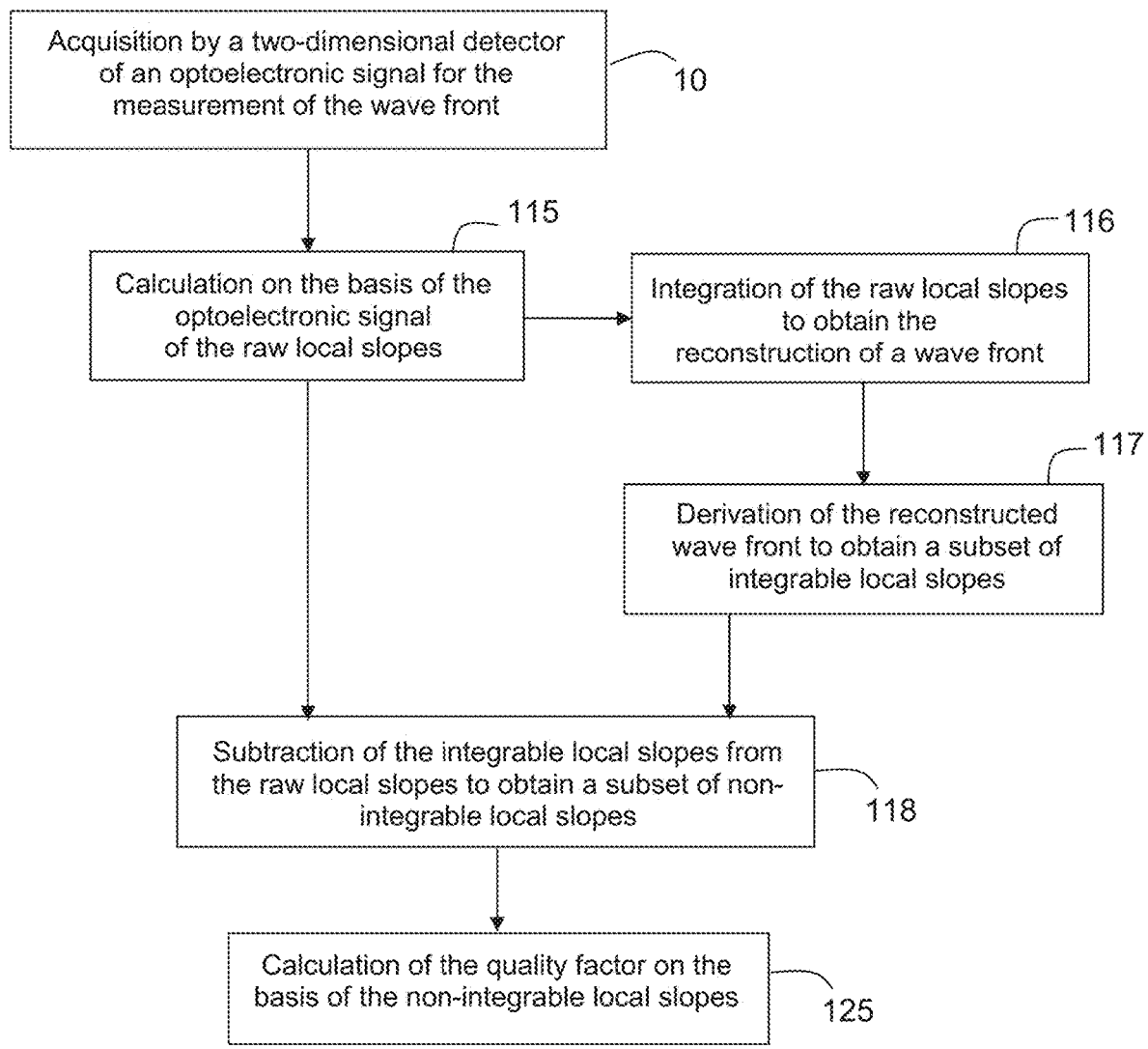
FIG. 4, a diagram illustrating steps of a second example of a method for evaluating the quality of the measurement of the optical wavefront according to this description.

FIG. 4 illustrates a second exemplary determination of a parameter characteristic of a parasitic signal component to evaluate the quality of the wavefront measurement. In this example, a parameter characteristic of a parasitic signal component includes a subset of the raw local slopes determined on the basis of the optoelectronic signal, formed by the non-integrable local slopes.

The applicant made the following observation; wavefront analyzers by direct measurement only have access to the wavefront derivative. These analysers can therefore only measure continuous wavefronts, i.e. wavefronts, the local slopes of which are 100% integrable. The identification and quantification of the local slopes that cannot be integrated into the measured local slopes is therefore an objective indicator of the quality of the implementation of the wavefront measurement. Indeed, a wavefront measurement performed under optimal conditions of implementation must give a set of non-integrable local slopes that are negligible or almost nil. On the other hand, there is no reason why the degradation due to a parasitic signal should have the property of being 100% integrable. It will therefore generate a subset of integrable slopes that will degrade the wavefront measurement and a subset of non-integrable slopes, the estimation of which will make it possible to determine a measurement quality factor. Indeed, the presence of non-integrable local slopes is an indicator of the presence of parasitic integrable local slopes, resulting from a parasitic signal, which will disturb the reconstruction of the wavefront desired to be analyzed.

Figure 5A:
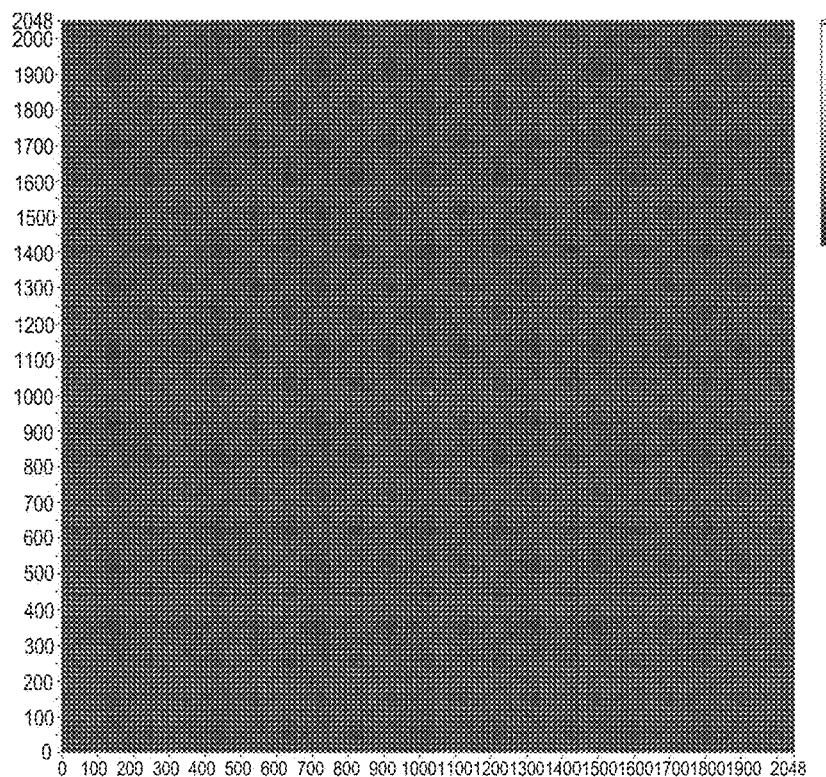
FIG. 5A, an example of an optoelectronic signal acquired by the detector of a wavefront analysis system, disturbed by parasitic interference.
Figure 5B:
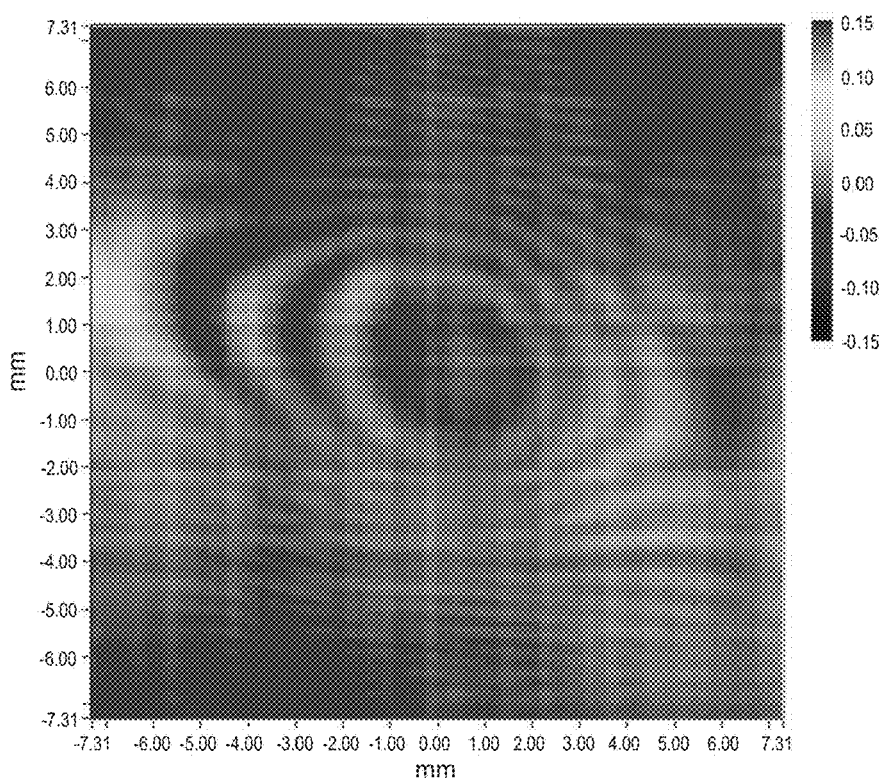
FIG. 5B the wavefront after integration of all the raw local slopes, themselves calculated by the wavefront analysis system on the basis of the optoelectronic signal shown on FIG. 5A.
Figure 6A:
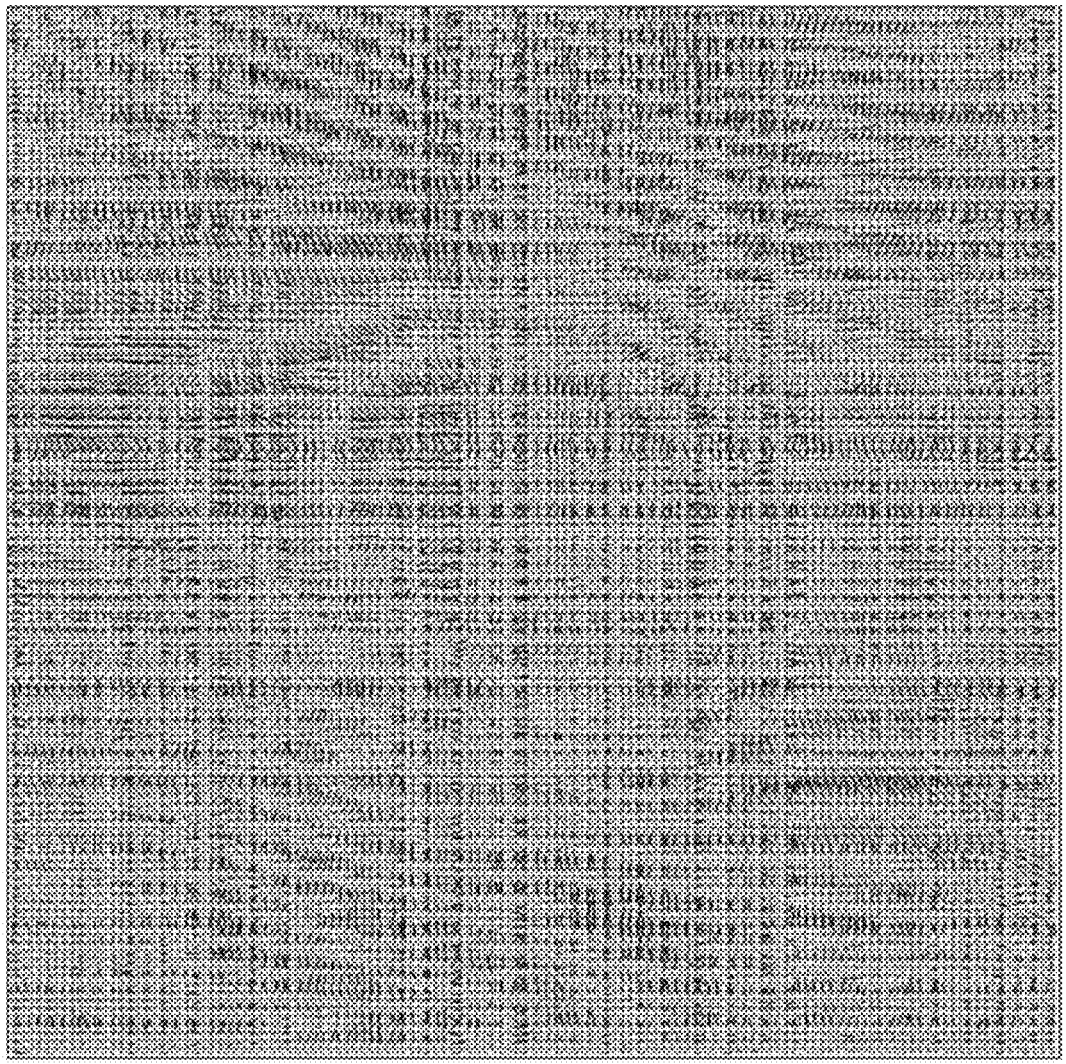
FIGS. 6A-6C of the images illustrating respectively the set (FIG. 6A) of the raw local slopes of the wavefront calculated on the basis of the optoelectronic signal represented on FIG. 5A, the set (FIG. 6B) of the local integrable slopes of the wavefront calculated on the basis of a derivation of the wavefront (represented on FIG. 5B), the set (6C) of the non-integrable local slopes of the wavefront calculated on the basis of the subtraction of the set of integrable local slopes of the wavefront (FIG. 6B) to all raw local slopes (FIG. 6A).
Figure 6B:
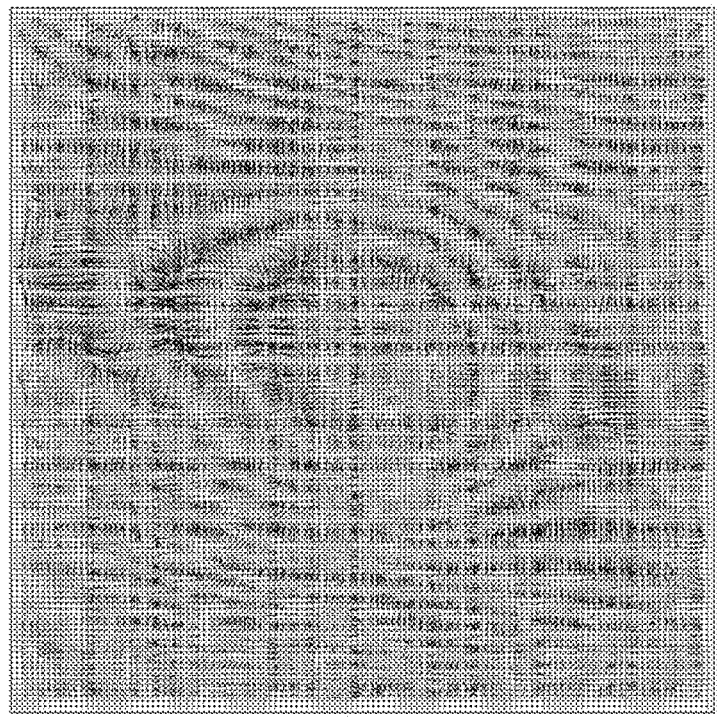
Figure 6C:
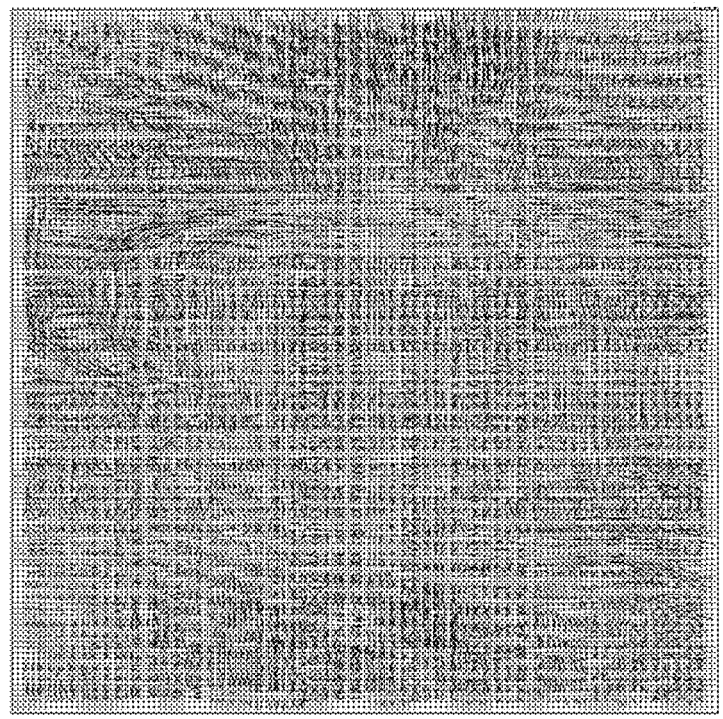

For example, FIG. 5A represents the optoelectronic signal obtained with a Hartmann Shack analyzer, comprising 128× 128 microlenses. This analyzer measures the phase of an optical wavefront passing through a blade with flat and parallel faces, one face of which has a semi-reflective coating and the other face is not coated. The illumination beam is monochromatic at a wavelength of 1064 nm and the coherence length of the illumination beam is much greater than the thickness of the blade. The signal is therefore disturbed by a parasitic wave generated by the double reflection on both sides of the blade and this parasitic wave interferes with the beam that has passed through the blade. The contrast of this interference is very low and this interference is difficult to detect on the optoelectronic signal from the matrix detector. However, the effect of this interference is clearly visible on the result of the wavefront measurement (FIG. 5B) and generates a measurement error twice as high as the accuracy of the wavefront analyzer. FIG. 6A represents the map of the raw local slopes calculated on the basis of the optoelectronic signal shown in FIG. 5A. FIG. 6B represents the map of the integrable local slopes obtained through a digital derivation of the wavefront shown in FIG. 5B and FIG. 6C the map of the non-integrable local slopes, the results of the difference between the raw local slopes and the integrable local slopes. FIGS. 6A, B and C are displayed at the same scale for the representation of the local slopes. It can immediately be noted that the effect of interference generates non-integrable local slopes of significant amplitude (of the same order of magnitude as the amplitude of the integrable local slopes). To simplify the display of local slope data, it has been chosen to display these as vectors, the standard and direction of which are calculated on the basis of the 2 slope tables along x and y.

Figure 7A:
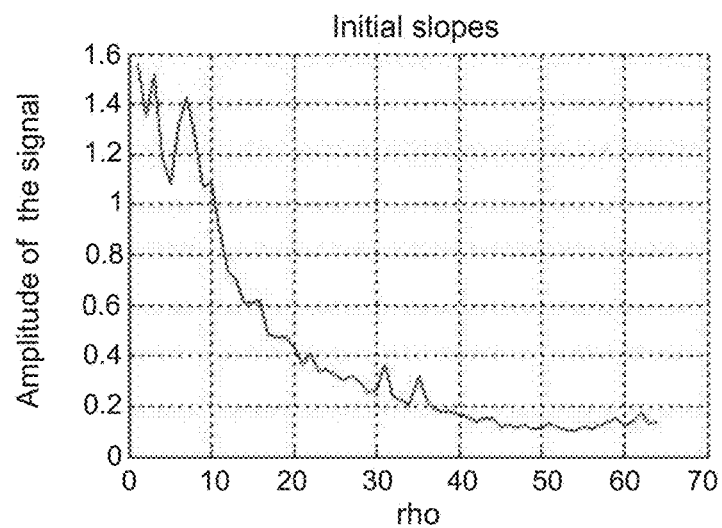
FIGS. 7A-7C, diagrams showing respectively the power spectral density of the raw local slopes (FIG. 7A), of the local integrable slopes (FIG. 7B) and of the local non-integrable slopes (FIG. 7C).
Figure 7B:
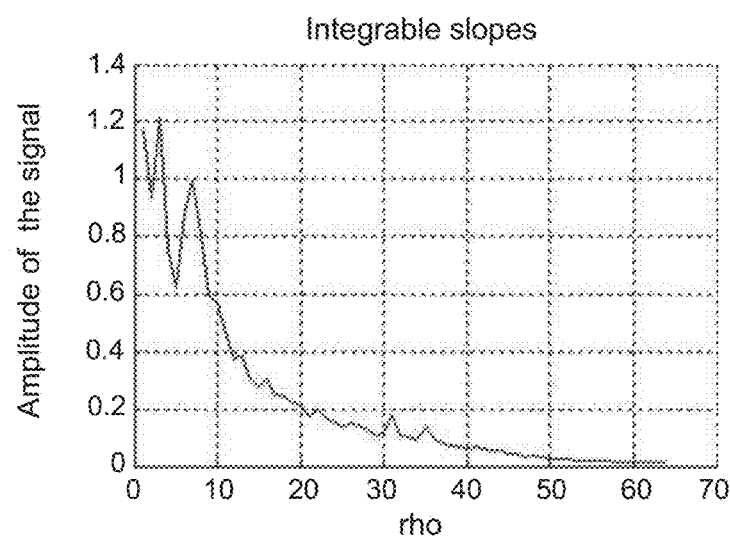
Figure 7C:
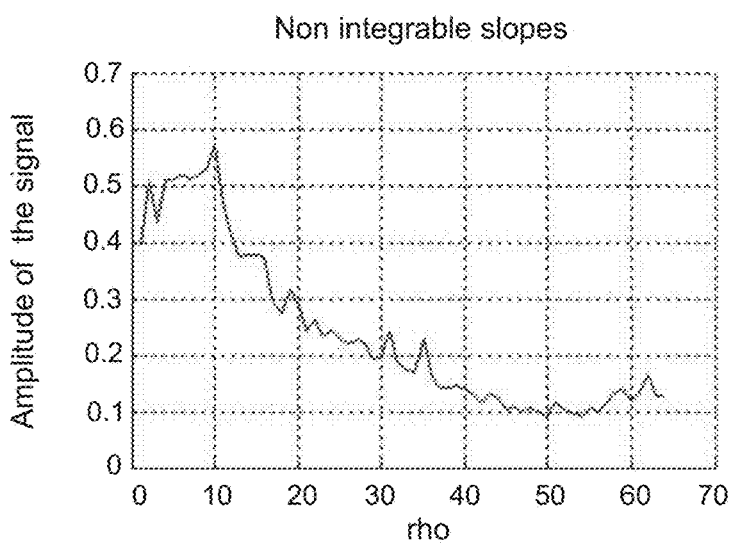

FIGS. 7A, 7B and 7C respectively represent the power spectral density (PSD) of the raw local slopes along the x axis (FIG. 7A), the local slopes that can be integrated along the x axis (FIG. 7B) and the local slopes that cannot be integrated along the x axis (FIG. 7C). These figures are obtained respectively from the table of local slopes along the x axis, of raw local slopes, of local integrable slopes and of local non-integrable slopes. The power spectral density is obtained by calculating the square of the Fourier transform modulus of the local slope tables along the x axis. The result of this calculation gives a power density table and each of the displayed curves is the result of the integration of the power spectral density table for each spatial frequency. The same calculation can of course be made from the local slope tables along the y axis.

According to an exemplary embodiment, the calculation of the quality factor from the non-integrable local slopes (step 125 of FIG. 4) can be achieved by simply calculating for example the RMS value of the table of non-integrable local slopes along the x axis, the RMS value of the table of non-integrable local slopes along the y axis and averaging the 2 RMS values found. A higher value of the quality factor indicates a more disturbed measurement. Of course, the quality factor can be calculated in many other ways.

For example, according to an exemplary embodiment, the calculation of the quality factor can take into account the frequency behaviour (spatial frequency) of the local slopes that cannot be integrated. Indeed, the information the user is looking for is wavefront information, i.e. the result of the integration of the measured local slopes (the raw local slopes). However, the amplitude of the re-injection of the local slope errors on the wavefront during the integration depends on the spatial frequency of the local slope errors: the low spatial frequency errors generate, during integration, high wavefront errors while the high spatial frequency errors generate low wavefront errors. Since the frequency behaviour of the integrable local slopes errors and that of the non-integrable local slopes are similar, the frequency study of the non-integrable slopes makes it possible to refine our knowledge of the importance of the degradation of the wavefront measurement. In particular, a predominant weight can be given to the low spatial frequencies of the slopes that cannot be integrated in the calculation of the measurement quality factor. For example, the weight may be the inverse of the spatial frequency, or it may be decided to keep for the calculation of the quality factor only those slopes the spatial frequency of which is less than a fraction of the cut-off frequency.

According to one exemplary embodiment, the calculation of the quality factor (Q) carried out on the basis of the non-integrable local slopes (step 125 of FIG. 4) can be carried out as follows:

Let the integrated power spectral densities (DSP) such as those of FIG. 7A-7C for the local slopes that cannot be integrated along the x-axis and the y-axis be noted DSPix and DSPiy.

Let the maximum spatial frequency up to which the frequency content of the DSP is to be taken into account be noted fmax. For example, if it is desired to favour low spatial frequencies when calculating the quality factor, fmax can be set at ¼ of the cut-off frequency of the DSPix or DPSiy (in the case of FIG. 7, the cut-off frequency is 64).

In this case, the quality factor Q is worth:

$$Q = \frac{\sum_{\rho=1}^{fmax} DSPix(\rho) + \sum_{\rho=1}^{fmax} DSPiy(\rho)}{2}$$

In this example, it can be considered that the quality of the measurement is excellent if Q is smaller than 1 and very bad if Q is above 20.

According to another exemplary embodiment, the calculation of the quality factor (Q) carried out from the non-integrable local slopes (step 125 of FIG. 4) can be carried out as follows:

DSPix and DSPiy are the integrated DSPs such as those in FIG. 7A-7C of the local slopes that cannot be integrated along the x-axis and y-axis.

Let the cut-off frequency of the DSPix or DPSiy (in the case of FIG. 7, the cut-off frequency is 64) be noted fc.

The quality factor Q is worth:

$$Q = \frac{\sum_{\rho=1}^{fc}(DSPix(\rho)/\rho) + \sum_{\rho=1}^{fc}(DSPiy(\rho)/\rho)}{2}$$

In this example, it can be estimated that the quality of the measurement is excellent if Q is smaller than 0.25 and very bad if Q is above 5.

Again, the previous example has been described for a Shack-Hartmann analyzer, but it can be transposed to any one of the wavefront analyzers by direct measurement.

As before, a display of the "measurement quality" can then be made. For example, colours or numbers are associated with calculated values of the quality factor, indicating to the user what each colour or number corresponds to. Thus, for example, there can be 5 levels of the quality factor, corresponding respectively to excellent, good, average, bad, very bad quality. Depending on the level of the quality factor, a user may be recommended a number of measures to be taken to restore better measurement conditions. When the level of quality is not satisfactory, several improvements can be brought. For example:

Eliminate the ambient light (switch off the light in the room where the measurement is performed)

Hide the parasitic light sources that may, even partially, illuminate the detector of the wavefront analyzer. These parasitic light sources may be a computer monitor, on/off indicators of electronic devices, a desk lamp, etc.

Acquire a background image that will be subtracted from the acquisitions made to measure the wavefront. One way to acquire a background image is to acquire an image with the detector of the wavefront analyzer by turning off or hiding the light source generating the beam used to perform the measurement (source 24 of FIG. 2 for example).

Place a filter hole for parasitic light in a beam focusing plane used to perform the measurement if such a plane exists. This action is particularly useful for "double pass" measurements in a reflective system.

Decrease the temporal coherence of the source when possible in order to reduce any risk of interference.

It is of course possible to combine the use of several parameters characteristic of the parasitic component of the optoelectronic signal to calculate the measurement quality factor. For example, the final quality factor of the measurement could result from multiplying a quality factor calculated using the method described in relation to FIG. 3A with a quality factor calculated using the method described in relation to FIG. 4.

Although described though a number of detailed exemplary embodiments, the method for evaluating the quality of the measurement of an optical wavefront, as well as the systems for analyzing a wavefront by direct measurement implementing such a method, comprise different alternative embodiments, modifications and improvements which will be obvious to those skilled in the art, its being understood that these different alternative embodiments, modifications and improvements fall within the scope of the invention as defined in the following claims.

In particular, the invention has been described using the example of a Shack-Hartmann but it can also be applied to Hartmann type systems, lateral shearing interferometer type systems, or more generally direct edge analyzer designed to measure the local slopes of a wavefront.

The invention claimed is:

1. A method for evaluating the quality of the measurement of an optical wavefront issued from an object to be characterized by a user, the method comprising:
   the acquisition of an optoelectronic signal, said optoelectronic signal resulting from the measurement by means of a wavefront sensor of the optical wavefront issued from said object to be characterized, said wavefront sensor comprising a two-dimensional detector;
   the determination on the basis of said optoelectronic signal of at least one parameter characteristic of a parasitic component of the optoelectronic signal;
   the evaluation of a quality factor of the measurement of the wavefront as a function of said at least one parameter characteristic of the parasitic component of the optoelectronic signal; and
   the display, using a display unit, to the user of a level of quality of the measurement as a function of said quality factor,
   wherein the determination on the basis of the optoelectronic signal of the parameter characteristic of the parasitic component of the optoelectronic signal comprises:
      calculating, on the basis of said optoelectronic signal, raw local slopes of the optical wavefront at a given number of points, and
      determining, for each raw local slope, a non-integrable component, thereby forming a subset of non-integrable local slopes.

2. The method for evaluating the quality of the measurement of an optical wavefront according to claim 1, wherein the determination of said subset of non-integrable local slopes comprises:
   the integration of said raw local slopes to obtain a reconstruction of a wavefront;
   the derivation of the thus reconstructed wavefront in order to determine, for each raw local slope, an integrable component, thus forming a subset of the integrable local slopes at each of said points;
   the subtraction at each of said points of the integrable local slopes with the raw local slopes to obtain said subset of the non-integrable local slopes.

3. The method for evaluating the quality of the measurement of an optical wavefront according to claim 1, wherein the quality factor is evaluated on the basis of a peak-valley value or a root mean square value (RMS) of at least a portion of said non-integrable local slopes.

4. The method for evaluating the quality of the measurement of an optical wavefront according to claim 1, wherein the quality factor is evaluated on the basis of a power spectral density (PSD) value of at least a portion of said non-integrable local slopes.

5. The method for evaluating the quality of the measurement of an optical wavefront according to claim 1, wherein the determination of a parameter characteristic of a parasitic component of the signal comprises the following steps:
   the identification of areas of the detector not covered by a signal useful for the measurement of the wavefront;
   the determination of the parameter characteristic of a parasitic component of the signal on the basis of the signal measured in said areas.

6. A method for analyzing an optical wavefront issued from an object to be characterized by a user, comprising:
   the acquisition of an optoelectronic signal, said optoelectronic signal resulting from the measurement by means of a wavefront sensor, of an optical wavefront issued from the object to be characterized, said wavefront sensor comprising a two-dimensional detector;
   the reconstruction of the wavefront on the basis of said optoelectronic signal to obtain a measurement of the wavefront;
   the determination on the basis of said optoelectronic signal of at least one parameter characteristic of a parasitic component of the optoelectronic signal;
   the evaluation of a quality factor of said measurement of the wavefront, as a function of said at least one parameter characteristic of the parasitic component of the optoelectronic signal; and
   the display, using a display unit, to the user of a level of quality as a function of said quality factor,
   wherein the determination on the basis of the optoelectronic signal of the parameter characteristic of the parasitic component of the optoelectronic signal comprises:
      calculating, on the basis of said optoelectronic signal, raw local slopes of the optical wavefront at a given number of points, and
      determining, for each raw local slope, a non-integrable component, thereby forming a subset of non-integrable local slopes.

7. A system for analyzing an optical wavefront by direct measurement, comprising:
   a wavefront sensor provided with a two-dimensional detector for the acquisition by a user of an optoelectronic signal allowing the measurement of the wavefront from an object to be characterized; and
   a signal processing unit for the reconstruction of the wavefront on the basis of said optoelectronic signal, said processing unit being further configured for:
      the determination, on the basis of said optoelectronic signal, of at least one parameter characteristic of a parasitic component of the optoelectronic signal;
      the evaluation of a quality factor of the measurement of the wavefront as a function of said at least one parameter characteristic of the parasitic component of the optoelectronic signal; and
   a display unit to the user of a level of quality of the measurement as a function of said quality factor,
   wherein the determination on the basis of the optoelectronic signal of the parameter characteristic of the parasitic component of the optoelectronic signal comprises:
      calculating, on the basis of said optoelectronic signal, raw local slopes of the optical wavefront at a given number of points and
      determining, for each raw local slope, a non-integrable component, thereby forming a subset of non-integrable local slopes.

8. The system for analyzing an optical wavefront by direct measurement according to claim 7, wherein the wavefront sensor comprises a matrix of microlenses, respectively holes, positioned in front of a two-dimensional detector and the optoelectronic signal comprises an array of spots formed by each of the microlenses, respectively the holes, illuminated by the wavefront to be measured.

9. The system for analyzing an optical wavefront by direct measurement according to claim 7, wherein the wavefront sensor comprises a phased array positioned in front of a two-dimensional detector and the optoelectronic signal comprises an array of spots formed by the figure resulting from the interference of the waves generated by the phased array through which the wavefront to be measured passes.

10. The method for evaluating the quality of the measurement of an optical wavefront according to claim 2, wherein the quality factor is evaluated on the basis of a peak-valley value or a root mean square value (RMS) of at least a portion of said non-integrable local slopes.

11. The method for evaluating the quality of the measurement of an optical wavefront according to claim 2, wherein the quality factor is evaluated on the basis of a power spectral density (PSD) value of at least a portion of said non-integrable local slopes.

12. The method for evaluating the quality of the measurement of an optical wavefront according to claim 3, wherein the quality factor is evaluated on the basis of a power spectral density (PSD) value of at least a portion of said non-integrable local slopes.

13. The method for evaluating the quality of the measurement of an optical wavefront according to claim 2, wherein the determination of a parameter characteristic of a parasitic component of the signal comprises the following steps:

the identification of areas of the detector not covered by a signal useful for the measurement of the wavefront;
the determination of the parameter characteristic of a parasitic component of the signal on the basis of the signal measured in said areas.

14. The method for evaluating the quality of the measurement of an optical wavefront according to claim 3, wherein the determination of a parameter characteristic of a parasitic component of the signal comprises the following steps:

the identification of areas of the detector not covered by a signal useful for the measurement of the wavefront;
the determination of the parameter characteristic of a parasitic component of the signal on the basis of the signal measured in said areas.

15. The method for evaluating the quality of the measurement of an optical wavefront according to claim 4, wherein the determination of a parameter characteristic of a parasitic component of the signal comprises the following steps:

the identification of areas of the detector not covered by a signal useful for the measurement of the wavefront;
the determination of the parameter characteristic of a parasitic component of the signal on the basis of the signal measured in said areas.

* * * * *